United States Patent [19]
Ersek

[11] Patent Number: 5,045,075
[45] Date of Patent: Sep. 3, 1991

[54] SURGICAL DRAIN APPARATUS AND METHOD

[75] Inventor: Robert A. Ersek, Austin, Tex.

[73] Assignee: Renoble, N. V. - Division 1, Austin, Tex.

[21] Appl. No.: 370,632

[22] Filed: Jun. 23, 1989

[51] Int. Cl.$^5$ .............................................. A61M 27/00
[52] U.S. Cl. ...................... 604/317; 604/93; 604/264; 138/119
[58] Field of Search .................. 604/255, 280, 317, 8, 604/93, 128, 264, 266, 247; 138/119, 137, DIG. 11

[56] References Cited

U.S. PATENT DOCUMENTS

| | | | |
|---|---|---|---|
| 3,295,556 | 1/1967 | Gertsma et al. | 138/119 |
| 4,445,897 | 5/1984 | Ekbladh et al. | 604/93 |
| 4,579,555 | 4/1986 | Russo | 604/282 |
| 4,784,651 | 11/1988 | Hickey | 604/93 |

FOREIGN PATENT DOCUMENTS 3525165  1/1987  Fed. Rep. of Germany ...... 604/280

Primary Examiner—Stephen C. Pellegrino
Attorney, Agent, or Firm—J. Nevin Shaffer, Jr.; Russell D. Culbertson

[57] ABSTRACT

A surgical drain system includes an elongated drain member having a conduit portion connected to a fluid intake portion with a fluid flow passage extending continuously through both portions and with at least one fluid intake opening in the fluid intake portion. The conduit portion of the drain member has generally a marquise-shaped transverse cross-section, whereas the fluid intake portion has a similar cross-sectional shape but absent the pointed end portions of the marquise shape. In use, the drain member may be positioned with the fluid intake portion within the wound in a desired position and with the conduit portion traversing the wound, and the wound edges may easily be made to conform to the marquise shape of the conduit portion to form a substantial seal. The drain member also preferably includes a one-way valve connected to the conduit portion for preventing fluid from flowing into the wound through the drain member. The drain system may also include a fluid receptacle adapted to be sealably connected to the drain member for receiving fluid drained from the wound, and the receptacle may be adapted to provide a suction to the drain member.

29 Claims, 3 Drawing Sheets

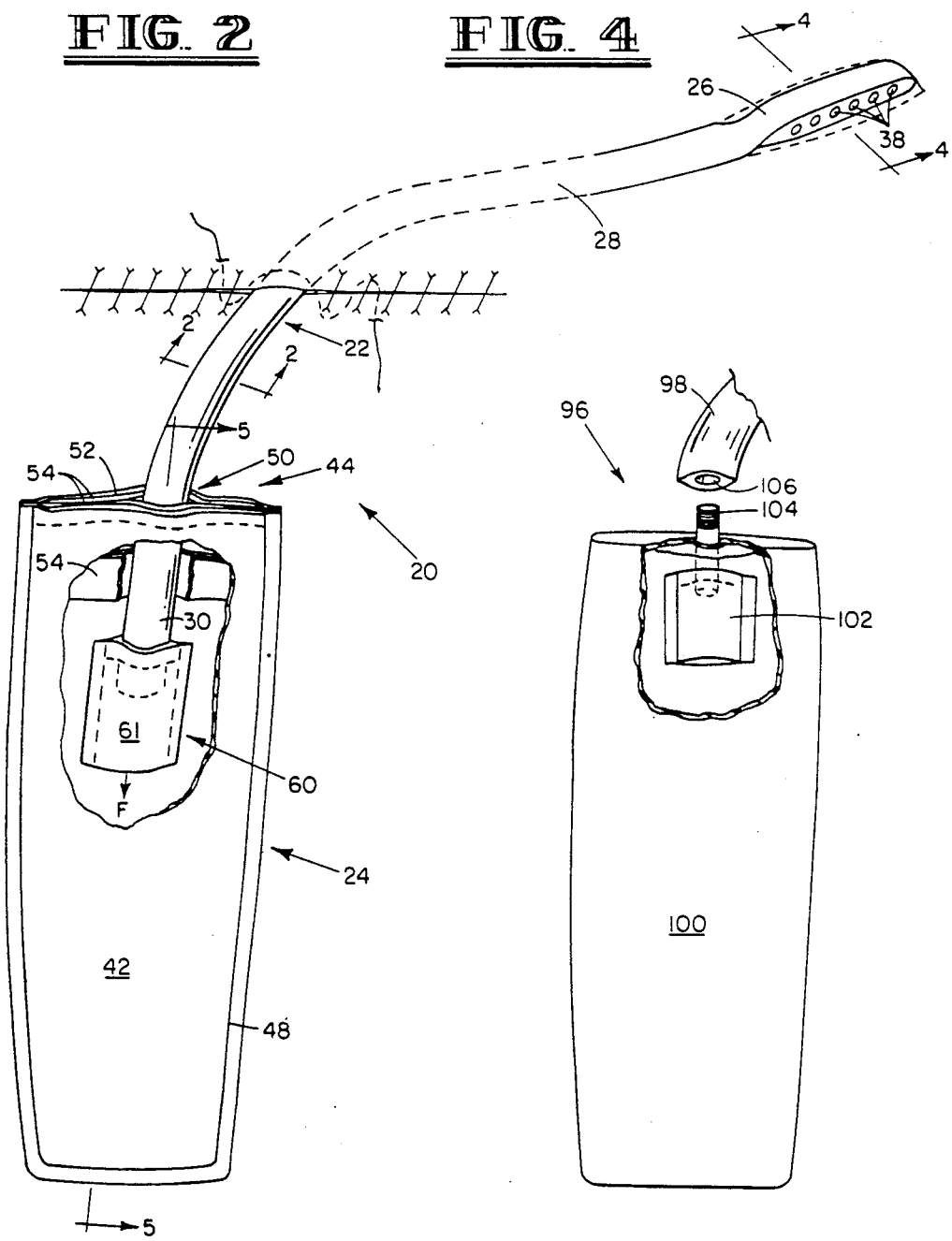

SURGICAL DRAIN APPARATUS AND METHOD

BACKGROUND OF THE INVENTION

This invention is related to surgical drains for use in draining fluid that may collect within a surgical wound, and more particularly, to a surgical drain apparatus and method for draining fluid from a wound while preventing contaminants from entering the wound and while preventing substantial leakage of drained fluid.

It is the present medical practice to place a drain in any surgical wound where contamination, trauma, excessive bleeding, or other factors may lead to the accumulation of serous fluid, blood, or pus within the wound. The purpose of surgical drains is to prevent the accumulation of surgical fluids and the toxic substances of degradation by allowing the fluids to exit the body.

There are principally two categories of surgical drains, passive drains and active drains. Both types of drains generally include an elongated drain member or tube and a fluid receptacle adapted to be connected to one end of the drain member for receiving the drained fluids. A drain member generally includes a fluid flow passage extending the length of the member for providing a path through which fluids exit the patient's body. A drain member also includes a fluid intake portion that is adapted to be inserted into the patient's body through a drain wound or incision and positioned inside the patient's body for receiving fluids that are likely to develop.

Typically, both categories of prior drain members were exited through a separate small drain wound made specifically for exiting the drain. The additional drain wound was used primarily because the wound could be sized for a tight fit with the drain member so as to reduce leakage between the wound and the drain member. The separate drain wound also provided an exit for the drain member without interfering with the healing of the primary surgical wound or incision.

Passive surgical drains generally include a drain member comprised of a thin walled tube or strip made of a suitable material such as rubber or flexible plastic. A passive drain simply prevents the wound edges or drain site incision edges from becoming adherent and provides a channel through which fluid may flow into or out of the wound.

Active surgical drains in addition to providing a channel through which fluids may exit the patient's body also include some means of applying negative pressure or suction to the drain member. The negative pressure or suction enhances the flow of fluids from the wound and also helps to dislodge small particles that may occasionally block the drain member flow passage. The negative pressure is usually applied with a spring activated bellows incorporated into the fluid receptacle. Some of these negative pressure receptacles also have anti-reflux or one-way valves to prevent fluids in the receptacle from flowing back into the wound.

There are also some differences in the drain members used in active as opposed to passive drain systems By contrast to the thin walled drain members used in passive drains, the drain member used in an active drain system must be relatively thick-walled to prevent the collapse of the flow passage under the applied negative pressure. Also, the intake portion of a drain member used in an active drain system often includes a number of small slits or holes along its length that enable fluids to enter the drain from a large area within the wound.

Although the intake portion of the drain members have been designed in a variety of transverse cross-sectional shapes or configurations, they are generally either round or rectangular. The rectangular-shaped drains are often described as being flat drains with the implication that some maximum amount of surface area for large flow can be achieved without distorting the tissues or organs that the drain member may pass. Also, regardless of the shape of the intake or inter-wound portion of the drain member, prior drain members have all included a generally round portion that is positioned at the host-prosthesis interface.

There are a number of problems associated with prior surgical drains. One such problem is that prior drain systems allowed contaminants to enter the wound either by back flow into the wound through the drain member or by leakage between the drain member and the drain wound edges. Leakage of fluids out of the wound between the drain member and the drain wound edges is another problem heretofore encountered in the use of surgical drains known in the art.

Leakage between the drain member and the drain wound occurs primarily because of gaps between the drain members previously used and the edges of the drain wound. In order to produce a lasting seal, the wound edges must be made to conform to the shape of the drain member with substantially no gaps at any point around the member. However, the drain wound made with a trochar or awl is always generally elliptical in shape whereas the portion of the prior drain members that traverses the wound was generally round in transverse cross-sectional shape. Although the rounded drain members or tubes could be passed via a small incision or wound through the skin and subcutaneous tissue in a very tight relationship, any seal obtained was temporary at best because of the pressure necrosis of the intervening tube through the wound. Also, even where the drain member fit very tightly through its own separate drain incision, a draining sinus tract usually developed over time that allowed the free egress of drained fluids from the wound and the ingress of skin contaminants and other bodily secretions from outside the wound.

Contaminants enter the drain wound through the drain tube itself not only in passive drains where there is no means to draw fluid to the receptacle, but also in prior active drains when negative pressure was removed from the drain tube such as when the receptacle was changed or drained. When a drain receptacle was drained or changed, it was generally disconnected from the drain member which stayed in place extending through the wound and into the patient's body. At disconnection, contaminants were sucked into the drain member flow passage through the disconnected open end of the drain member. The contaminants once in the drain member, could even flow into the wound if suction was not re-established fairly quickly to draw the contaminants out of the drain member and into the receptacle.

Another problem arose in the prior drains where the inter-wound or intake portion of the drain was rectangular with the remainder of the drain member having a round shape. Such drains were generally not integrally formed due to the two dissimilar shaped sections and there was generally a seam remaining where the two sections were joined. Not only was the junction of the two dissimilar drain member sections always a site of possible failure, but also the seam at the junction of the two sections and the change in shape itself caused substantial pain to the patient when the drain was pulled through the body tissues and out through the drain incision as the drain was removed.

BACKGROUND OF THE INVENTION

It is generally an object of the invention to provide a surgical drain apparatus and method that overcomes the problems and deficiencies associated with prior surgical drains mentioned above.

Particularly, it is an object of the invention to provide a surgical drain that may be exited through the major surgical wound or incision while maintaining a substantial seal at the host-prosthesis interface, that is, between the wound edges and the drain member where the drain member traverses the wound.

Another object of the invention is to provide a surgical drain for use in active drain systems that prevents the flow of contaminants into the drain when the drain is separated from the fluid receptacle and suction means.

A further object of the invention is to provide a surgical drain system that is simple to use, comfortable to the patient, and inexpensive to manufacture.

A surgical drain system according to the invention includes a uniquely shaped drain member and also a unique fluid receptacle. Specifically, the drain member has a transverse cross-sectional shape to which the wound edges of an awl or trochar produced wound, or even the edges of a linear incision, may be made to conform to produce a substantial and lasting seal. The drain member also preferably includes a one-way or check valve that prevents the flow of contaminants into the drain member's fluid flow passage when the drain member is disconnected from the fluid receptacle.

A drain member embodying the principles of the invention includes an elongated fluid intake portion connected at one end to an elongated conduit portion, the conduit portion having an outlet end opposite the end to which the fluid intake portion of the drain member is connected. A flow passage extends longitudinally through both the conduit portion and the fluid intake portion of the drain member. Also, the fluid intake portion includes at least one fluid intake opening for enabling fluid to flow into the flow passage at the fluid intake portion of the drain member.

According to the invention, the conduit portion of the drain member has a marquise-shaped transverse cross-section, that is, a generally lentricular elliptical shape but terminating in pointed ends along the major axis rather than rounded ends as in a true elliptical shape. The fluid intake portion of the drain member has a similar cross-sectional shape but preferably with the pointed ends along the major transverse axis removed.

In use, the drain member is positioned so that the entire fluid intake portion resides inside the patient's wound and so that the conduit portion traverses the incision or wound, with the major transverse axis of the marquise shape generally aligned with the major axis of the wound or incision. The edges of an awl or trochar produced wound or even the edges of the primary surgical incision may be made to conform snugly with the unique marquise shape of the drain member. Where the drain exit wound is large, perhaps the primary surgical wound, a substantial seal may be obtained between the incision edges and the drain member using a continuous subcutaneous stitch through the subcutaneous tissue with interrupted stitches on either side of the drain member. Alternatively, where the wound is small and made with an awl or other suitable instrument, the drain member may be sized so as to fit snugly through the wound so that a seal is formed between the drain member and the wound edges of the elliptical wound.

In a preferred form of the invention, the drain member includes a one way or check valve, preferably positioned at the outlet end of the conduit portion of the drain member. The one-way valve helps to prevent contaminants from entering the drain member particularly when the drain member is disconnected from the suction means and fluid receptacle. In one preferred form of the invention, the one-way valve is integrally formed with the conduit portion of the drain member at the outlet end of the conduit portion. In other embodiments, a suitable connector means is employed to connect the check valve to the drain member conduit portion, preferably at the outlet end thereof.

The drained fluid receptacle, pursuant to the invention, includes a reservoir bag with a suitable connector for sealably connecting the drain member to the reservoir bag and also preferably includes means for applying suction or negative pressure to the drain member. The preferred connector for connecting the drain member to the reservoir bag includes a linear slit or opening in the bag between two strips of material coated with a suitable adhesive on their opposing surfaces. The adhesive coated strips may be spread slightly to facilitate insertion of the outlet end of the drain member conduit portion, including the one-way valve, into the reservoir bag and then adhered against the conduit portion of the drain member. As with the seal at the drain incision, the marquise-shaped transverse cross-section of the drain member conduit portion enables the adhesive coated edges of the reservoir bag to form a good seal against the drain member with no gaps where leakage would occur. When the receptacle must be drained or changed, the drain member may be disconnected by separating the adhesive coated strips from the drain member and then withdrawing the drain member through the slit or opening.

BRIEF DESCRIPTION OF THE DRAWINGS

Other objects, features and advantages of the present invention will become more fully apparent from the following detailed description of the preferred embodiment, the appended claims and the accompanying drawings in which:

FIG. 1 is a view in perspective of a surgical drain system embodying the principles of the invention;

FIG. 2 is a view in transverse cross-section of the conduit portion of the drain member taken along line 2—2 in FIG. 1;

FIG. 4 is a view in transverse cross-section of the fluid intake portion of the drain member taken along line 4—4 in FIG. 1;

FIG. 11 is a view in perspective of an alternate surgical drain system embodying the principles of the invention.

BRIEF DESCRIPTION OF THE PREFERRED EMBODIMENTS

Figure 8:
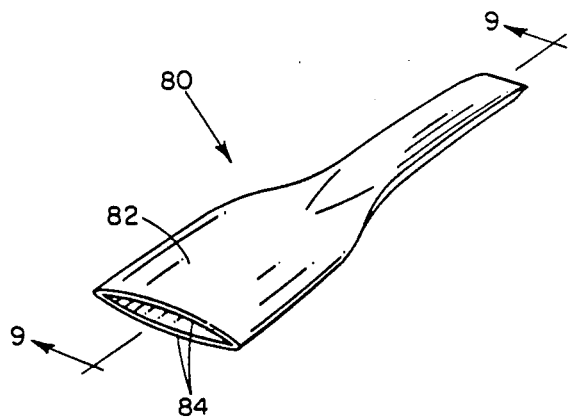
FIG. 8 is a view in perspective of another alternate preferred form of valve member.

Referring to FIG. 1, a surgical drain system 20 embodying the principles of the invention includes an elongated drain member 22 adapted to be connected to a fluid receptacle 24. The drain member 22 includes a fluid intake portion 26 connected at one end to a conduit portion 28, the conduit portion 28 having an outlet end 30 opposite the end to which the fluid intake portion 26 is connected. In the preferred form of the drain member 22 illustrated in FIG. 1, the conduit portion 28 and the fluid intake portion 26 are integrally formed from a single piece of suitable material such as silicone dioxane (silicon rubber) The integrally formed drain member eliminates any seam at the junction of the two drain member portions.

Figure 3:
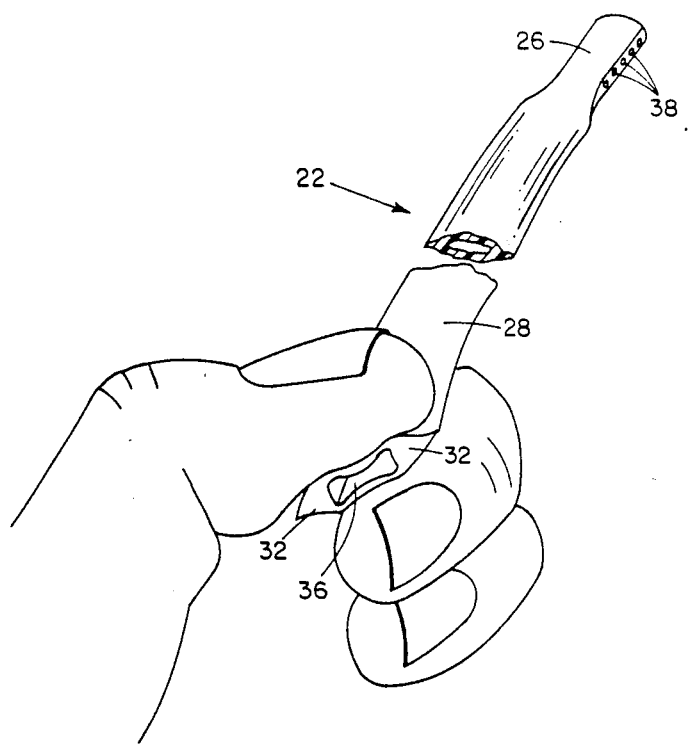
FIG. 3 is a view in transverse cross-section similar to FIG. 2, but with the conduit portion of the drain member pinched between two fingers.

FIGS. 2, 3, and 4 show the unique transverse cross-sectional shape of the drain member 22 according to the invention. As shown particularly in FIG. 2, the conduit portion 28 of the drain member 22 has a marquise-shaped transverse cross-section. That is, the transverse cross-sectional shape of the conduit portion 28 is generally elliptical but with the shape terminating along the major transverse axis, indicated by reference letter M, at pointed end portions 32 rather than rounded ends as in a true elliptical shape. Furthermore, the preferred shape of each of the end portions 32 shown in FIG. 2 includes a concave portion leading to, or adjacent to, the point of the end portion. Referring to FIG. 4, the fluid intake portion 26 of the drain member 22 has a marquise-shaped transverse cross-section similar to that of the conduit portion 28, but with the pointed end portions removed to form lateral surfaces, preferably channels 34, on either side of the fluid intake portion 26. It should be noted from the drawings that the only change in transverse cross-sectional shape from the conduit portion 28 of the drain to the fluid intake portion 26 is the absence of the pointed end portions 32 found along the conduit portion of the drain member.

The drain member 22 also includes a fluid flow passage 36, shown in FIGS. 2, 3, and 4, extending longitudinally through the drain member from the fluid intake portion 26 to the outlet end 30 of the conduit portion 28. In the preferred form, the fluid flow passage 36 has a generally oval or elliptical transverse cross-sectional shape along its entire length and is oriented so that its major transverse axis generally aligns with the major transverse axis M of the conduit portion 28 and also the fluid intake portion 26. As shown in FIG. 3, the preferred oval shape combined with the unique marquise shape of the drain member makes it difficult to accidentally pinch off the flow passage 36 so as to entirely block the flow through the drain member 22. Similarly, the drain member can withstand a substantial negative pressure within the fluid flow passage 36 without collapsing.

As shown best in FIGS. 1 and 4, the fluid intake portion 26 of the drain member 22 includes at least one, and preferably a plurality of, fluid intake openings 38 for enabling fluid to flow into the drain member flow passage 36 from the patient's body. In the preferred form of the invention, the openings 38 extend through the walls 40 of the drain member fluid intake portion from the lateral channel surfaces 34 to the fluid flow passage 36. In use the oblong, modified marquise shape of the fluid intake portion helps to separate body tissues allowing maximum access of any collected fluid to the laterally positioned fluid intake openings 38. Also, in the preferred form of the invention, the fluid intake openings 38 are each slightly smaller than the fluid flow passage 36 extending through the drain member 22. The openings 38, being smaller than the fluid flow passage 11. 36, help prevent material from entering the fluid flow passage that might block the flow of fluid. The use of many small openings 38 thus helps to ensure an open drainage path even though some of the openings may be blocked during use.

Figure 5:
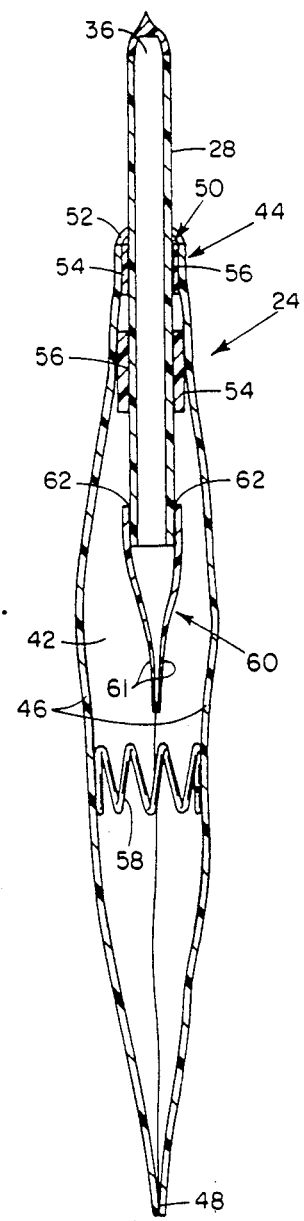
FIG. 5 is a view in longitudinal cross-section of the drain fluid receptacle and the valve member, taken along line 5—5 in FIG. 1.

Referring to FIGS. 1 and 5, the fluid receptacle 24 is adapted for receiving and collecting fluids that are drained from a patient's body through the drain member 22. In the illustrated preferred form of the invention the fluid receptacle 24 includes a fluid collection reservoir or bag 42 formed from a suitable flexible material, preferably a suitable plastic, and also includes connector means 44 for sealably connecting the drain member 22 to the bag. The bag or reservoir 42 may be formed from two sheets 46 of flexible material sealed by any suitable means at their edges 48 as shown, or alternatively, the bag 42 may be formed from a single sheet of plastic (not shown) by a suitable process.

The connector 44 in this preferred form of the invention includes a slit or opening 50 in the bag 42 preferably along a connecting edge 52 of the bag. Two strips 54 of flexible material coated with an adhesive 56 on their opposing surfaces are connected to the bag 42 on either side of the opening 50. The adhesive coatings may be preserved when not in use by suitable cover material such as glazed paper (not shown). Also, in alternate forms of the invention, the strips may each have several separate bands of adhesive coating, one band on each strip being used each time a seal is desired.

To connect the illustrated preferred drain member to the fluid receptacle 24, the outlet end 30 of the drain member conduit portion 28 may be inserted a short distance through the opening 50 and then each of the strips 54 sealed with the adhesive coating 56 against the marquise-shaped conduit portion 28. The strips 54 can easily conform to the marquise shape of the conduit portion to form a water-tight and air-tight seal as shown in FIGS. 1 and 5. Also, the drain member can be disconnected easily by peeling the adhesive coated strips 54 from the conduit portion 28 so that the outlet end 30 can be withdrawn.

A surgical drain embodying the principles of the invention can be used as a passive drain, having a simple receptacle with no means for applying a suction or negative pressure to the drain member. However, the illustrated preferred form of the invention includes suction means, integrated with the receptacle 24, for producing the required negative pressure for active draining. In this form of the invention, the suction means includes a biasing member 58 mounted within the bag or reservoir 42 and adapted to bias the opposing sides 46 of the bag apart. When the biasing member 58 is compressed, the volume of the bag 42 is lowered with the two sides of the bag relatively close together. The compressed biasing member 58 produces a bellows action forcing the sides 46 of the bag 42 apart and tending to draw fluid into the bag through the opening 50 or through the drain member 22 when connected as in FIG. 1.

The drain member 22 illustrated in FIG. 1 also includes means, in this case a one-way or check valve 60, for preventing the flow of fluid through the fluid flow passage 36 from the outlet end 30 of the drain member conduit portion 28 to the fluid intake portion 26, while allowing flow in the opposite direction indicated by arrow F in the FIGURES. The one-way valve 60 prevents the flow of contaminants into the outlet end 30 of the drain member 22 when the drain member is disconnected from the receptacle 24 and suction means. In this form of the invention the one-way valve 60 includes two of sheets 61 of a thin, flexible material. The sheets 61 are connected together at their side edges and are open at both ends. Adhesive strips 62 are provided at one open end for enabling the valve 60 to be sealingly connected to the outlet end of 30 of the drain member 22 as shown in FIGS. 1 and 5.

In use, the preferred valve 60, being connected to the outlet end 30 of the drain member conduit portion 28, is positioned and sealed within the reservoir 42 of the fluid receptacle. In this position, the thin flexible sheets 61 may part to allow flow or seepage in the direction F. However, the sheets 61 are forced together creating an effective seal in response to even a slightly higher pressure in the area inside the reservoir 42, which higher pressure would otherwise cause fluid to flow through the valve 60 in the direction opposite to arrow F.

Figure 6:
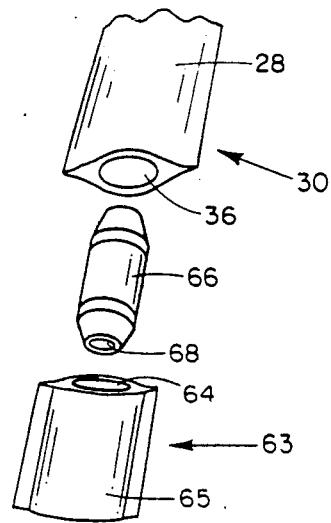
FIG. 6 is an exploded view in perspective showing one preferred form of valve member and conduit portion connection.

Referring to FIG. 6, an alternate preferred one-way valve 63 includes a connector end 64 and a flow control portion 65. A suitable friction connector 66 with a flow passage 68 may be used to sealably connect the connector end 62 of the valve to the fluid flow passage at the outlet end 30 of the drain member conduit portion 28. The flow control portion 65 of the one-way valve 60 includes two thin sheets of flexible material sealed together along their side or lateral edges so as to form a flow path therebetween. The two sheets operate similarly to the sheets 61 shown in FIGS. 1 and 5 to prevent the flow of fluid into the outlet end 30 of the drain member conduit portion 28, 22 while allowing flow in the opposite direction.

Figure 7:
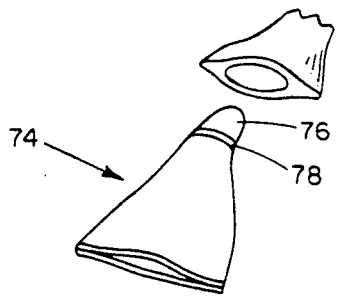
FIG. 7 is a view in perspective of an alternate preferred form of valve member.
Figure 9:
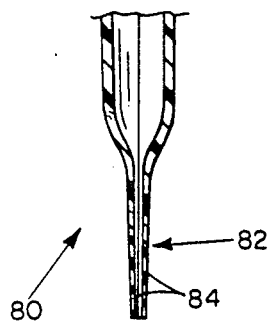
FIG. 9 is a view in longitudinal cross-section taken along line 9—9 in FIG. 8.

In the alternate form of one-way valve 74 shown in FIG. 7, the connector member 76 is formed integrally with the connector end 78 of the check valve. Still another alternate preferred form of one-way valve 80 is shown in FIGS. 8 and 9. In this form, the one-way valve 80 is integrally formed with the drain member at the outlet end thereof. As with the embodiment shown in FIGS. 1, 5, and 6, the integrally formed one-way valve 80 includes a flow control portion 82 comprised of two thin flexible sheets 84 which operate similarly to those shown at 61 in FIGS. 1 and 5.

Figure 10:
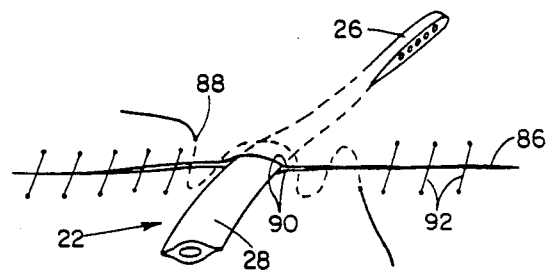
FIG. 10 is a somewhat schematic view in perspective of a surgical drain embodying the principles of the invention in position for draining fluid from within a patient's wound.

The preferred method of draining fluid from a wound 86 may be described with particular reference to FIG. 10. The method includes first providing a marquise-shaped drain member 22 as described above, and then positioning the drain member so that the fluid intake portion 26 is inside the wound 86 in the desired position for receiving fluid through the fluid intake openings 38 and so that the conduit portion 28 traverses the wound 86, that is, so that the conduit portion is positioned at the host-prosthesis interface. Once the drain member is positioned, the method continues with the step of applying a continuous subcutaneous stitch 88 through the subcutaneous tissue at the wound edges 90 so as to draw the edges against the conduit portion 28 of the drain member 22. Next, interrupted stitches 92 are applied to further draw the wound edges 90 against the drain member conduit portion 28. As shown in FIG. 10, the proper stitching makes the wound edges 90 conform to the marquise-shaped transverse cross-section of the drain member conduit portion 28 to form a substantial seal.

After a seal is formed by applying the stitching 88 and 92, the method may continue with the steps of providing a suitable fluid receptacle 24 as described above with respect to FIG. 1 and then sealably connecting the receptacle to the outlet end 30 of the drain member 22 so that fluid may flow from the wound 86 through the drain member and collect in the receptacle reservoir 42. In the preferred form of the invention, the fluid receptacle also includes suction means, preferably including the biasing member 58 (FIG. 5), and the method includes applying a suction or negative pressure to the drain member 22 to urge fluid from the wound 86.

Particularly where the drain member of the invention is used as a passive drain, it may be desirable to apply a peristaltic action to the drain member to help drain fluid from the wound and to help move fluid through the drain member. Although suitable for use in active drain systems without collapsing from the applied negative pressure, the marquise-shaped drain member when made from a suitable flexible and resilient material and when fitted with a suitable one-way valve, also easily accommodates a gentle peristaltic motion. Furthermore, where the drain member material is sufficiently resilient, the drain member may be partially collapsed to provide its own suction or negative pressure to urge fluid into the fluid intake openings of the drain member. Such suction is particularly useful in draining residual fluid from the wound as the drain member is removed.

FIG. 11 shows an alternate surgical drain system 96, according to the invention, including a marquise-shaped drain member 98, similar to the drain member 22 of FIG. 1, and a fluid receptacle 100. In this alternate form of the invention, a one-way check valve 102 is incorporated into the fluid receptacle 100, in contrast to the drain member mounted check-valve, 60, 74, and 80 illustrated in FIGS. 5, 7, and 8, respectively. The fluid receptacle 100 also includes a suitable friction connector 104 adapted to be inserted into the drain member flow channel 106 for connecting the drain member 98 to the receptacle.

While the present invention has been disclosed in connection with the preferred embodiments thereof, it should be understood that there may be other embodiments which fall within the spirit and scope of the invention as defined in the following claims.

What is claimed is:

1. A surgical drain comprising:
   A. an elongated conduit portion having an outlet end and a marquise-shaped transverse cross-section, the conduit portion being adapted for transversing a wound with the major transverse axis of the marquise shape aligned with the wound so that the wound edges may conform to the marquise-shaped conduit portion and create a seal around the entire transverse perimeter of said conduit portion;

B. an elongated fluid intake portion connected to the end of said conduit portion opposite said outlet end and being adapted to be positioned within a patient's body through the wound;

C. a fluid flow passage extending longitudinally through said conduit portion and said fluid intake portion of the drain, the fluid flow passage being adapted for enabling fluid to flow through said fluid intake portion and said conduit portion and out said outlet end of said conduit portion; and D. at least one fluid intake opening in said fluid intake portion of the drain for enabling fluid to flow into said fluid flow passage.

2. The surgical drain of claim 1 wherein said conduit portion of the drain and said fluid intake portion are integrally formed.

3. The surgical drain of claim 2 wherein said fluid intake portion has a generally marquise-shaped transverse cross-section but with the pointed ends along the major transverse axis removed, and wherein the marquise shape of said fluid intake portion is generally aligned with the marquise shape of said conduit portion.

4. The surgical drain of claim 3 including a plurality of fluid intake openings extending into said fluid flow passage so as to enable fluid to flow into said flow passage, said fluid intake openings being spaced out along the length of said fluid intake portion and being generally aligned with the major transverse axis of said fluid intake portion.

5. The surgical drain of claim 4 wherein each of said fluid intake openings is smaller than said fluid flow passage extending through said conduit portion and said fluid intake portion of the drain.

6. The surgical drain of claim 5 wherein said fluid flow passage has generally an elliptical shape with the major transverse axis of the elliptical shape generally aligning with the major transverse axis of the marquise shape of said conduit portion and fluid intake portion of the drain.

7. The surgical drain of claim 1 including valve means for preventing substantial flow of fluid through said fluid flow passage from said conduit portion to said fluid intake portion while allowing fluid flow in the opposite direction.

8. The surgical drain of claim 7 wherein said valve means is a suitable one-way valve.

9. The surgical drain of claim 8 wherein said one-way valve is positioned at the outlet end of said conduit portion.

10. The surgical drain of claim 9 wherein said one-way valve includes two aligned sheets of flexible material, the sheets being sealably connected at one end to the outlet end of said conduit portion, and being sealably connected together at their lateral edges so as to form a flow path between said two sheets through which fluid may exit said conduit portion, whereby fluid may flow from said conduit portion of the drain member through said flow path defined between said two sheets, but the pressure required for fluid flow in the opposite direction forces said two sheets together to prevent the flow of fluid into said conduit portion of the drain member through the outlet end.

11. The surgical drain of claim 10 wherein said one-way valve is integrally formed with said conduit portion of the drain.

12. The surgical drain of claim 10 including connector means for sealably connecting said one-way valve to the outlet end of said conduit portion.

13. The surgical drain of claim 12 wherein said connector means includes a suitable friction connector.

14. The surgical drain of claim 1 wherein said conduit portion and said fluid intake portion are made of a suitable silicone rubber material.

15. A surgical drain system comprising:

A. an elongated surgical drain member having a conduit portion and a fluid intake portion connected together and also having a fluid flow passage extending longitudinally through both said conduit portion and said fluid intake portion, said conduit portion having a marquise-shaped transverse cross-section and said fluid intake portion having a similar marquise-shaped transverse cross-section but with the pointed end portions of the marquise shape being removed and also having at least one fluid intake opening through which fluid may flow into said fluid flow passage extending through said fluid intake portion; and B. a fluid receptacle having a fluid collection reservoir and connector means for sealably connecting with said conduit portion of the drain member so that fluid may flow from said fluid flow passage of the drain member into said fluid collection reservoir, whereby the drain member may be positioned for draining fluid through a suitable drain wound with said fluid intake portion within a wound, said conduit portion traversing the wound, and with the wound edges pressed against said conduit portion of the drain member so as to form a seal between the drain member and the wound, and whereby fluid may drain from the wound through said fluid flow passage of the drain member and into said fluid collection reservoir without substantial leakage between the drain member and the wound edge.

16. The surgical drain system of claim 15 wherein said flow passage has generally an elliptical transverse cross-section having its major transverse axis generally aligned with the major transverse axis of said conduit and fluid intake portions of the drain member.

17. The surgical drain system of claim 16 wherein said fluid intake portion of the drain member includes a plurality of fluid intake openings, each opening being smaller than said fluid flow passage and being aligned generally with the major transverse axis of said fluid intake portion.

18. The surgical drain system of claim 17 wherein the drain member includes valve means for substantially preventing the flow of fluid from said conduit portion of the drain member to said fluid intake portion.

19. The surgical drain system of claim 18 wherein said valve means is a suitable one-way valve.

20. The surgical drain system of claim 19 wherein said one-way valve is adapted to connected to said conduit portion of the drain member at the end opposite the end connected to said fluid intake portion.

21. The surgical drain system of claim 20 wherein said one-way valve includes two aligned sheets of flexible material each being sealably connected at one end to said conduit portion of the drain member, being sealably connected together at their lateral edges, and being open at the end generally opposite the end connected to said conduit portion so as to form a flow path therebetween, whereby the two sheets of material are forced together in response to a pressure gradient that would otherwise tend to cause fluid flow into the drain member through said conduit portion.

22. The surgical drain system of claim 21 wherein said one-way valve is formed integrally with the drain member.

23. The surgical drain system of claim 21 wherein said one-way valve is formed with the fluid receptacle.

24. The surgical drain system of claim 19 wherein said fluid receptacle includes suction means for providing a suction to said fluid flow passage of the drain member so as to urge fluid into said flow passage through said fluid intake openings.

25. The surgical drain system of claim 24 wherein said fluid collection reservoir may be expanded so as to increase its volume, and wherein the suction means includes a biasing member associated with said fluid collection reservoir for biasing the reservoir toward an expanded position so as to create a vacuum within the reservoir.

26. The surgical drain system of claim 15 wherein said connector means comprises:
   A. an opening in said fluid collection reservoir adapted for receiving said conduit portion of the drain member; and
   B. a strip of material connected to said reservoir along each side of the opening, each strip having an adhesive coating extending the length thereof, the adhesive coated strips being adapted for sealing against said conduit portion of the drain member when said conduit portion is received through the opening in said fluid collection reservoir.

27. A method of draining fluid that may develop within a surgical wound, said method comprising the steps of:
   A. providing an elongated surgical drain member having a conduit portion and a fluid intake portion with a fluid flow passage extending longitudinally through both said conduit portion and said fluid intake portion, said conduit portion having a marquise-shaped transverse cross-section and including an outlet end, and said fluid intake portion having a generally marquise-shaped transverse cross-section but with the lateral pointed edges of the marquise shape being removed and also having at least one lateral opening through which fluid may flow into said fluid flow passage extending through said fluid intake portion;
   B. positioning the drain member with said fluid intake portion within a wound in the desired position for collecting fluid, and with said conduit portion traversing the wound, the major transverse axis of the conduit portion being aligned generally with an incision for said wound;
   C. applying at least one subcutaneous continuous stitch through subcutaneous tissue with the stitch material looping around said conduit portion of the drain member traversing the wound so that said subcutaneous stitch pulls the opposing sides of the incision against said marquise-shaped conduit portion of the drain member to substantially seal against said conduit portion;
   D. applying interrupted stitches along the wound on both sides of the drain member so as to further draw the wound edges against the drain member; and
   E. sealably connecting a suitable fluid receptacle to the outlet end of said drain member conduit portion so that the receptacle may receive fluid drained from the wound through the drain member, whereby fluid may drain from within the wound into said fluid intake portion of the drain member and then through said conduit portion of the drain member out of a patient's body and into said drained fluid receptacle.

28. The method of claim 27 including the step of applying a negative pressure to the drain member to assist the flow of fluid into the drain member and from the drain member to the receptacle.

29. The surgical drain of claim 1 wherein the marquise-shaped transverse cross-section includes a concave portion adjacent to the pointed ends of said marquise shape.

* * * * *